(12) United States Patent
Wilson et al.

(10) Patent No.: US 11,786,121 B2
(45) Date of Patent: Oct. 17, 2023

(54) SYSTEM AND METHOD FOR MEASURING CARDIORESPIRATORY RESPONSE

(71) Applicants: UTI LIMITED PARTNERSHIP, Calgary (CA); THE GOVERNORS OF THE UNIVERSITY OF ALBERTA, Edmonton (CA)

(72) Inventors: Richard Wilson, Calgary (CA); Nicholas Jendzjowsky, Calgary (CA); Robert Herman, Calgary (CA); Willis Tsai, Calgary (CA); Fiona Costello, Calgary (CA); Craig Steinback, Edmonton (CA)

(*) Notice: Subject to any disclaimer, the term of this patent is extended or adjusted under 35 U.S.C. 154(b) by 761 days.

(21) Appl. No.: 16/609,893

(22) PCT Filed: May 3, 2018

(86) PCT No.: PCT/CA2018/050526
§ 371 (c)(1),
(2) Date: Oct. 31, 2019

(87) PCT Pub. No.: WO2018/201253
PCT Pub. Date: Nov. 8, 2018

(65) Prior Publication Data
US 2020/0196862 A1 Jun. 25, 2020

Related U.S. Application Data

(60) Provisional application No. 62/500,837, filed on May 3, 2017.

(51) Int. Cl.
*A61B 3/12* (2006.01)
*A61B 3/00* (2006.01)
(Continued)

(52) U.S. Cl.
CPC .......... *A61B 3/1241* (2013.01); *A61B 3/0025* (2013.01); *A61B 3/102* (2013.01); *A61B 3/1233* (2013.01); *A61B 5/4035* (2013.01)

(58) Field of Classification Search
CPC ..... A61B 3/1241; A61B 3/0025; A61B 3/102; A61B 3/1233; A61B 5/4035
See application file for complete search history.

(56) References Cited

U.S. PATENT DOCUMENTS

| 6,325,511 | B1* | 12/2001 | Mizuochi | A61B 3/1241 351/206 |
| 2006/0100528 | A1* | 5/2006 | Chan | A61B 3/102 600/476 |

(Continued)

OTHER PUBLICATIONS

Shiga, Yukihiro, et al. "Relative flow volume, a novel blood flow index in the human retina derived from laser speckle flowgraphy." Investigative ophthalmology & visual science 55.6 (2014): 3899-3904. (Year: 2014).*

(Continued)

*Primary Examiner* — Sean D Mattson
(74) *Attorney, Agent, or Firm* — Moore & Van Allen, PLLC; Henry B. Ward, III

(57) ABSTRACT

Systems and methods for use in measuring sympathetic nervous system activity or blood vessel autoregulation corrected for sympathetic activity. The choroid in the human eye is imaged and, using the resulting image, the vascular perfusion density (VPD) in the choroid is measured. VPD provides a measurement that is directly related to sympathetic nervous system activity. The effect of stimuli on sympathetic nervous system activity can be measured by comparing pre-stimuli VPD measurements with post-stimuli measurements. Quantifying VPD can be performed by determining pixel density within specific areas of the choroid image. Altered sympathetic nervous system activity can be (Continued)

detected in a subject by comparing that subject's VPD measurements to baseline VPD measurements from healthy individuals. Blood vessel autoregulation can be measured by imaging changes in other blood vessels in the eye and correcting with choroid VPD measurements of sympathetic activity.

15 Claims, 22 Drawing Sheets

(51) Int. Cl.
A61B 5/00 (2006.01)
A61B 3/10 (2006.01)

(56) References Cited

U.S. PATENT DOCUMENTS

| 2007/0195269 A1* | 8/2007 | Wei | A61B 3/102 351/221 |
| 2013/0301008 A1* | 11/2013 | Srivastava | G06T 11/003 351/246 |
| 2014/0180129 A1* | 6/2014 | Kostenich | A61B 5/489 600/476 |
| 2017/0296049 A1* | 10/2017 | Uji | G06V 40/19 |
| 2018/0360307 A1* | 12/2018 | Oh | A61B 5/0066 |

OTHER PUBLICATIONS

Pechauer, Alex D., David Huang, and Yali Jia. "Detecting blood flow response to stimulation of the human eye." BioMed research international 2015 (2015). (Year: 2015).*

International Search Report & Written Opinion dated Jul. 31, 2018, for corresponding PCT Application No. PCT/CA2019/050526, 7 pages.

Sander, B., "The Influence of the Autonomic Nervous System on the Human Choroid", 2017, 305 pages.

* cited by examiner

Subject A
(34 year old
athletic
male)

Subject B
(54 year old
sedentary
male)

Baseline

A

B

Hyperoxia

A

B

Hyperventilation

A            B           10s

Breath hold

A

B

Breath hold

Hypoxia

A

B

Hypercapnia

A

B

Cold pressor

A

B

10s

SYSTEM AND METHOD FOR MEASURING CARDIORESPIRATORY RESPONSE

TECHNICAL FIELD

The present invention relates to optical coherence tomography (OCT). More specifically, the present invention relates to methods and systems for using OCT to determine sympathetic nervous system activity in living humans or other animal species.

BACKGROUND

Most organs and blood vessels in the body receive inputs from the sympathetic nervous system. Altered sympathetic nervous system activity occurs as a consequence of drug administration/exposure, psychological and physiological stress (including hemorrhage) and disease. For example, alteration in sympathetic nervous system activity occurs during anaesthesia, in obesity, diabetes, hypertension, hypotension, asthma, chronic obstructive pulmonary disease (COPD), inflammation, anxiety/depression, sleep apnea, and other major cardiorespiratory and metabolic diseases. The consequences of sympathetic activity extend to all aspects of autonomic control and include direct hemodynamic effects such as changes in heart rate, blood pressure and/or regional distribution of blood flow to various vascular beds and organs, or other pathways involving inflammation, growth factors such as insulin and VEGF that contribute to vascular remodelling and atherosclerosis. In addition, most blood vessels are capable of autoregulation, adjusting their calibre according to their immediate environment. Autoregulation is subject to many of the same diseases and conditions above, but measurements of autoregulation in vivo are made difficult by the effects of sympathetic inputs. As such, assessment of sympathetic nervous system activity, and disentangling the effects of sympathetic activity from autoregulation on vascular beds, are potentially warranted for treatment of all diseases that involve altered sympathetic activity, all phases of drug discovery and use, and assessment of physiological and psychological stress.

Currently, measurement of sympathetic nervous system activity in biopharmaceutical research and development and in clinical settings is difficult to do and difficult to interpret. An effective and time-sensitive method for assessing sympathetic nervous system activity is urgently needed. The simplest of measurements of sympathetic nervous system activity may involve measuring the variation of beat-to-beat cardiac R-R intervals. However, the dual parasympathetic and sympathetic innervation of cardiac tissue clouds the ability to differentiate parasympathetic or sympathetic influence. Other techniques such as measurement of norepinephrine concentrations in blood or urine lack sensitivity and temporal resolution of moment-by-moment changes in hemodynamic function, and reproducibility may be compromised due to tissue re-uptake and clearance of noradrenaline. While these drawbacks have been overcome by the use of radiolabeled techniques and the direct delivery into specific tissues (cardiac and renal), these modifications further complicate routine use. One other option is to directly record nervous system activity. Indeed, the direct recording of sympathetic nervous system activity from sympathetic nerves using microneurography has long been the gold standard of sympathetic nervous system measurement. This technique possesses good sensitivity and reproducibility to measure real-time changes in sympathetic nervous system activity within subjects. However, the amplitude of nerve recordings cannot be easily compared between subjects due to differences in needle proximity within the nerve and inter-subject burst amplitude. In addition, discomfort associated with needle placement is likely to affect sympathetic nervous system activity itself and, in some cases, induce a strong vaso-vagal response that again compromises interpretation. Given the caveats associated with these techniques, their invasive nature, mixed success rate, and the need for additional measures to corroborate the effect of sympathetic nervous system activity, a feasible alternative to these techniques is needed.

There is therefore a need for systems and/or methods which address the above issues and which mitigate if not overcome such issues.

SUMMARY

The present invention provides systems and methods for use in measuring sympathetic nervous system activity. The choroid in the human eye is accurately imaged and, using the resulting image, the vascular perfusion density (VPD) in the choroid is measured. VPD provides a measurement that is directly related to sympathetic nervous system activity. The effect of stimuli on sympathetic nervous system activity can be measured by comparing pre-stimuli VPD measurements with post-stimuli measurements. Quantifying VPD can be performed by determining pixel/voxel density within specific regions of the choroid image. Heightened sympathetic nervous system activity can be detected in a subject by comparing that subject's VPD measurements over time and/or to baseline VPD measurements from healthy individuals.

In a first aspect, the present invention provides a system for measuring an effect of a stimulus to an autonomic nervous system of a human, the system comprising:
  an imaging device for imaging at least one portion of a human eye, said imaging device producing at least one image of said at least a portion of said human eye;
  a data storage device for storing said image;
  wherein
  said data storage device stores said at least one image from said imaging device;
  said at least one portion comprises choroid vasculature of said human eye;
  said system is used to obtain at least one first measurement in said choroid vasculature prior to an application of said stimulus to said human and to obtain at least one second measurement in said choroid vasculature subsequent to said application of said stimulus;
  a comparison of said first measurement to said second measurement indicating an effect of said stimulus on said autonomic nervous system.

In a second aspect, the present invention provides a system for determining a level of autonomic nervous system activity in a human, the system comprising:
  an imaging device for imaging at least one portion of a human eye, said imaging device producing at least one image of said at least a portion of said human eye;
  a data storage device for storing said image;
  wherein
  said data storage device stores said at least one image from said imaging device;
  said at least one portion comprises choroid vasculature of said human eye, said at least one image allowing for a measurement in said choroid vasculature;
  said system is used to obtain at least one measurement in said choroid vasculature;

said at least one measurement is compared with at least one previously obtained measurement to determine a level of said autonomic nervous system activity.

In a third aspect, the present invention provides a system for determining sympathetic nervous system activity in a human, the system comprising:
an imaging device for imaging at least one portion of a human eye, said imaging device producing at least one image of said at least one portion of said human eye;
a data storage device for storing said image;
wherein
said data storage device stores said at least one image from said imaging device;
said at least one portion comprises choroid vasculature of said human eye;
properties of said at least one image is indicative of vascular perfusion density in said choroid vasculature such that said properties is directly related to said sympathetic nervous system activity.

In a fourth aspect, the present invention provides a method for determining an amount of autonomic nervous system activity in a human, the method comprising:
obtaining at least one image of at least one portion of an eye of said human;
determining a measurement of a characteristic in said eye from said image;
comparing said measurement to a previously obtained measurement to determine if said autonomic nervous system activity is increased or decreased.

In a fifth aspect, the present invention provides a method for determining an amount of autoregulation in a human, the method comprising:
obtaining at least one image of at least one portion of a human eye;
determining measurements of two characteristics in said human eye from said image, said two characteristics being subject to different levels of autoregulation and sympathetic regulation; and
comparing said measurements to determine if said autoregulation is increased or decreased.

BRIEF DESCRIPTION OF THE DRAWINGS

The embodiments of the present invention will now be described by reference to the following figures, in which identical reference numerals in different figures indicate identical elements and in which.

DETAILED DESCRIPTION

Figure 1:
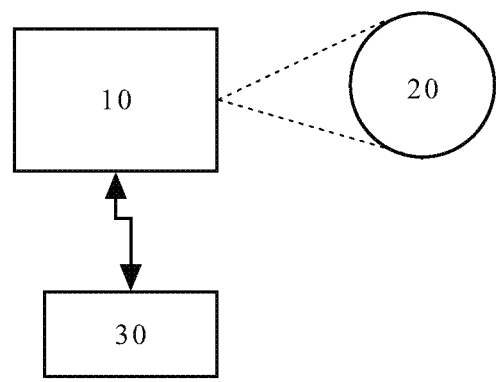
FIG. 1 is a block diagram of a system according to one aspect of the invention.

As is well-known, the choroid is richly innervated by the sympathetic nervous system and vaso-regulation is mediated by both $\alpha$- and $\beta$-adrenergic receptors (this is in contrast to blood vessels in the retina that receives weak sympathetic inputs). The choroid vasculature appears to be reactive to isometric exercise, postural changes and hypoxia, all of which increase activity of the sympathetic nervous system. Importantly, since the sympathetic nervous system regulates blood flow, vessel diameter, and cardiac output, then by measuring blood flow, one may attain an altered index of sympathetic activity. Vascular perfusion density (VPD) is a static measurement of total blood volume in the choroid (~ml) and in the choroid, sympathetic activity dominates autoregulation in determining blood vessel diameter. Therefore, measuring VPD (which is dictated solely by vessel diameter) provides an indirect measurement of sympathetic nervous system activity that is minimally affected by competing signals or other physiological indications. VPD can be measured by imaging the human eye and then isolating or focusing on the choroid. A section of the choroid can then be further analyzed by determining voxel/pixel properties (e.g., intensity) in the image. These voxel/pixel properties provide a measure of VPD and can be compared with the voxel/pixel properties of other regions in the image and with regions in similar images. Such a comparison effectively compares VPD between subjects and, in effect, compares sympathetic nervous system activity between different subjects. Similarly, by comparing the VPD for the same subject at different instances in time, the effect of treatments or of circumstances on a subject's sympathetic nervous system activity can also be compared. By comparing different regions of the eye, differentially affected by autoregulation and sympathetic innervation in this way, the effects of autoregulation and sympathetic activity can be disentangled: Sympathetic activity and/or autoregulation corrected for sympathetic activity can be assessed.

It should be noted that using stimuli to increase or decrease sympathetic activity specifically isolates changes due to sympathetic nervous system activity. The imaging of choroid vasculature in combination with physiologic, psychologic and/or pharmacologic stimuli to stimulate the sympathetic nervous system creates an accurate, reliable, and time-sensitive tool which can be used by researchers and clinicians to measure sympathetic nervous system reactivity.

In one embodiment, the present invention involves the use of optical coherence tomography (OCT) to image choroid vasculature in the eyes of an individual. The acquired images are analyzed and, by comparing the analyzed images with previously acquired images, one can quantify the reactivity of sympathetic nervous system to cardiorespiratory relevant stimuli or to other interventions. In one implementation, optical coherence tomography equipment is repurposed for non-invasive, expedient yet comprehensive, and low-cost human sympathetic nervous system monitoring and cardiovascular risk assessment. This new use for the OCT platform may have a significant impact on drug research and development in general, while revolutionizing biopharmaceutical research and development for diseases involving altered sympathetic nervous system activity and/or autoregulation.

Referring to FIG. 1, a block diagram of one aspect of the invention is provided. An imaging device 10 is used to capture images of a human eye 20. These images are then stored in a storage medium 30. As noted above, the imaging device is, preferably, a device which uses optical coherence tomography technology for imaging the eye. Other technologies which are based on optical interferometry may also be used. Other types of OCT-based technologies may also be used with the present invention. Specifically, OCT—EDI, swept—source OCT (SS—OCT) and image averaging OCT may also be used with the present invention.

In one implementation, a human eye was imaged using OCT equipment. The equipment used was a ZEISS Cirrus HD-OCT 4000 (Cirrus HD-OCT or Cirrus) device which enabled examination of the posterior and anterior of the eye at an extremely fine spatial scale, without surgical biopsy or even any contact with the eye. Using spectral domain optical coherence tomography, the Cirrus HD-OCT device acquires OCT data about 70 times faster (27,000 vs. 400 A-scans per second) and with better resolution (5 μm vs. 10 μm axial resolution in tissue), compared to earlier generation OCT technology such as a Stratus OCT device, also manufactured by Carl Zeiss Meditec. Cirrus acquires whole cubes of OCT image data, composed of hundreds of line scans, in about the same time as a Stratus OCT device acquires a six-line scan. These data cubes can be viewed in three planes or through three dimensions, thereby providing access to an extensive amount of retinal image data in one scan. Experimental results indicate that Fourier Domain OCT devices are eminently suited for use in the provision of highly reliable, 3D ocular images such that their spatial and temporal resolutions are sufficient to measure changes in choroid microvascular responses to sympathetic nervous system provocation or stimuli. The system and method of the present invention can be used for routine assessment of the choroid microvasculature and its sympathetic regulation in humans.

Figure 2:
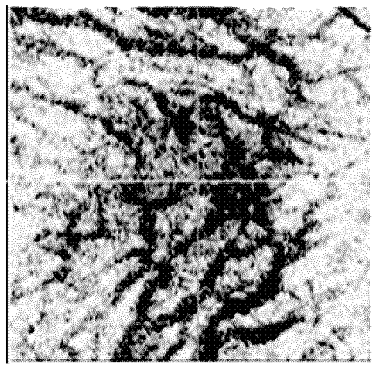
FIG. 2 is an image of the choroid subsequent to the Valsalva manoeuvre.
Figure 2:
Figure 2:
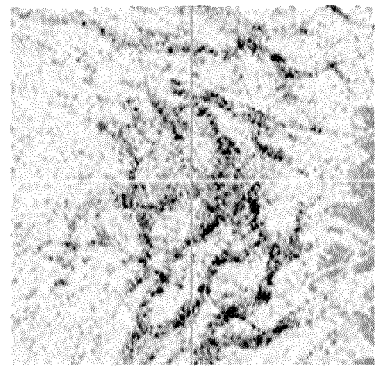
Figure 2:
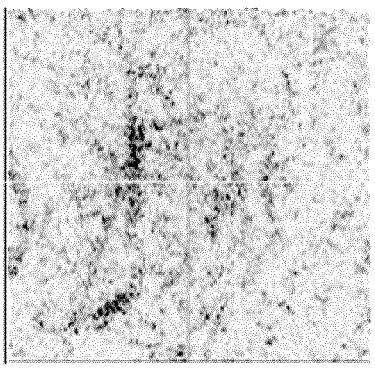
Figure 2:
Figure 2:
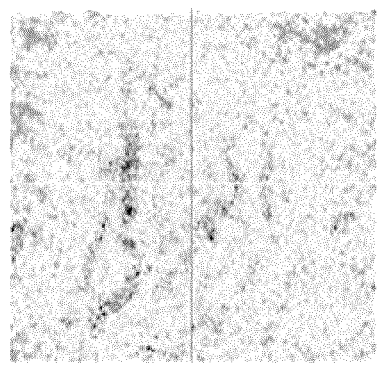
Figure 2:
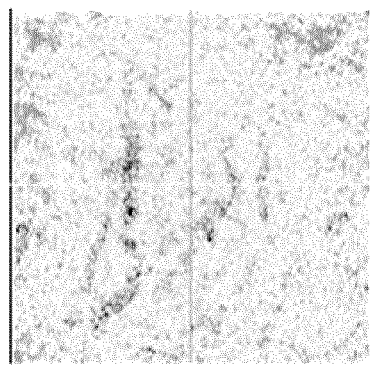

To demonstrate the effectiveness of the present invention, images of the choroid from two males were taken before and after sympathetic nervous system provocation (see FIG. 2). One subject (35 years old and an extreme athlete) had high choroid VPD, whereas the other (48 years old, sedate and newly-diagnosed as hypertensive) had low VPD. Two repeats for the 48-year old subject indicates that OCT yields stable measurements of VPD. After 15s of a specific stimulus (Valsalva manoeuvre-mediated sympathetic provocation), both males exhibited pronounced decreases in choroid VPD (meaning an increase in sympathetic nervous activity).

Figure 3:
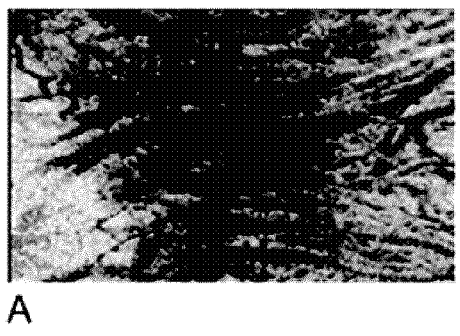
FIG. 3 is an image of a choroid prior to any stimuli or provocation to the sympathetic nervous system.
Figure 3:
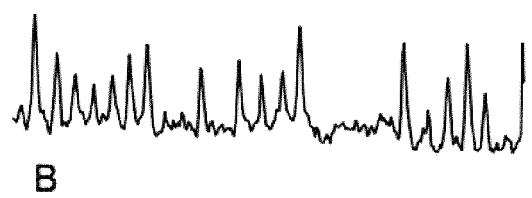

Referring to FIG. 3, an image of a choroid obtained using OCT is illustrated. This image provides a baseline for comparison with the other choroid images noted below. In addition to the image of the choroid, a plot of the sympathetic nervous system activity during the period the image was taken is provided at the right of FIG. 3. The image of the choroid in FIG. 3 was taken prior to any stimuli or provocation to the sympathetic nervous system.

Figure 4A:
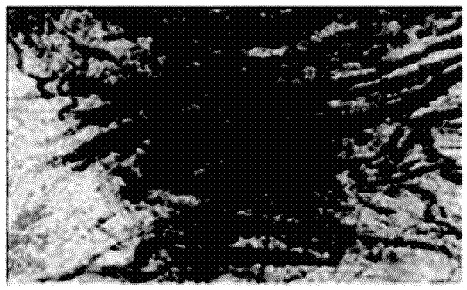
FIGS. 4A-4B are images of the choroid subsequent to different stimuli and illustrating an increased VPD.
Figure 4A:
Figure 4B:
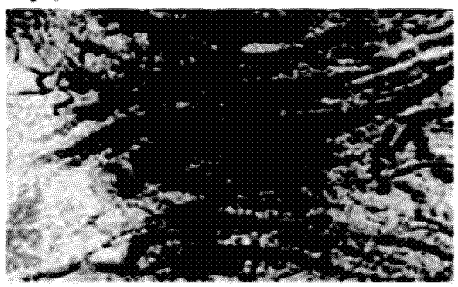
Figure 4B:
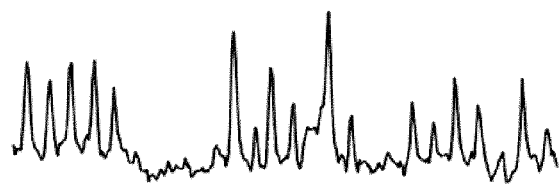

Referring to FIGS. 4A and 4B, illustrated are images of a choroid subsequent to stimuli or provocations that are known to reduce sympathetic nervous system activity. As with FIG. 3, to the right of each Figure is a plot of the sympathetic nervous system activity during the period when the image of the choroid was taken. FIG. 4A illustrates the microvasculature of the choroid after hyperoxia (high oxygen) while FIG. 4B illustrates the microvasculature of the choroid after hyperventilation. As can be seen, qualitatively, the amount of dark areas in FIG. 3 is less than in FIGS. 4A and 4B. Concurrent qualitative decreases in sympathetic activity (reduction of upward deflections) have occurred as can be seen from the traces in the Figures.

Figure 5A:
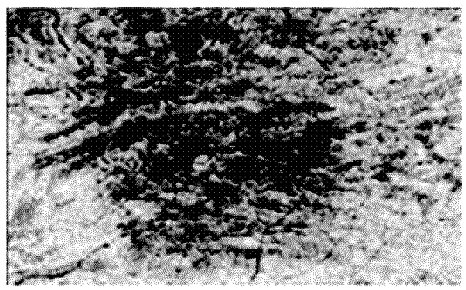
FIG. 5A-5D are images of the choroid subsequent to different stimuli and illustrating a decreased VPD.
Figure 5A:
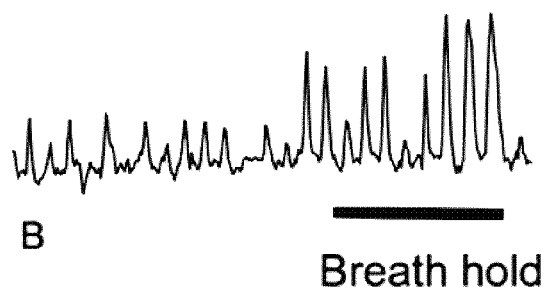
Figure 5B:
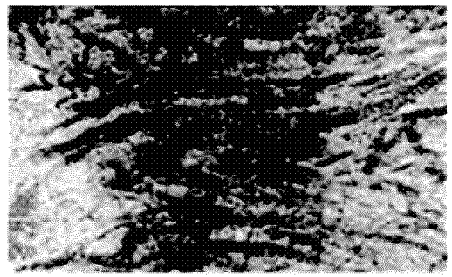
Figure 5B:
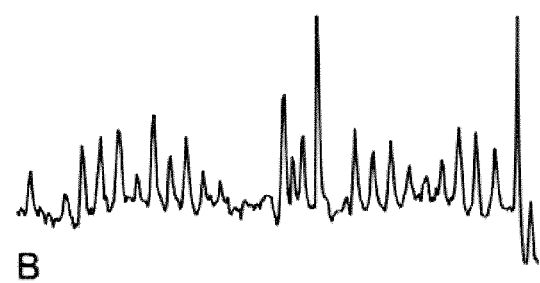
Figure 5C:
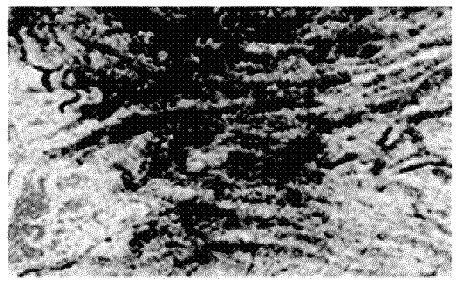
Figure 5C:
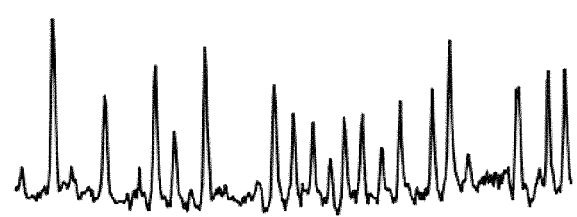
Figure 5D:
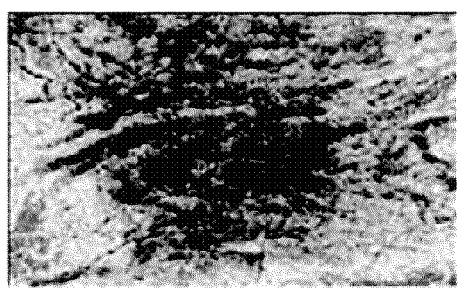
Figure 5D:
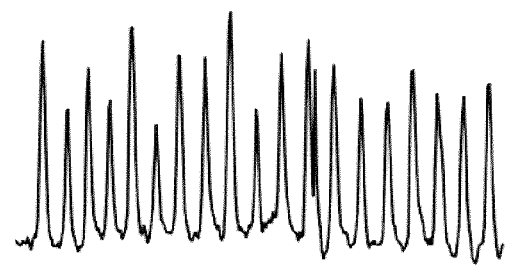
Figure 5D:

Referring to FIGS. 5A-5D, illustrated are images of a choroid subsequent to other stimuli or provocations. FIGS. 5A-5D are images of the choroid after stimuli that are known to increase sympathetic nervous system activity and thereby decrease choroid VPD. As with the previous Figures, to the left of the image of FIGS. 5A-5D are plots of sympathetic nervous system activity during the period when the images were taken. FIG. 5A illustrates the choroid after an end-expiratory breath hold where the subject holds his/her breath (known to stimulate the sympathetic nervous system). FIG. 5B illustrates the choroid after hypoxia (low oxygen). FIG. 5C illustrates the choroid after hypercapnia (high carbon dioxide), and FIG. 5D is an image of the choroid after a cold pressor (pain-based) provocation to the sympathetic nervous system. As can be seen, qualitatively, the image of FIG. 3 is darker than those of FIGS. 5A-5D. For greater clarity, stimuli and provocations (and protocols using these stimuli) which may be used on the sympathetic nervous system to confirm results are as follows:

1) Hyperoxia/hypoxia (high/low oxygen): hypoxia stimulates the sympathetic nervous system by exciting the chemical sensors in the carotid body (peripheral chemoreflex), leading to lower choroid VPD. Hyperoxia diminishes sympathetic nervous activity (and thereby increases choroid VPD) by the same mechanism but in the opposite direction. To obtain the necessary post stimulus scans, imaging of the choroid would be obtained during the last minute of a 3-5 minute bout of hyperoxic/hypoxic breathing.

2) Hypercapnia (high carbon dioxide) stimulates the chemical sensors in the brainstem (central chemoreflex). This stimulus increases the sympathetic nervous system activity, leading to lower choroid VPD. Scans of the choroid are taken in the last minute of a 3-5 minute bout of hypercapnia.

3) Hyperventilation: The only way to expel carbon dioxide is through hyperventilation. This stimulus serves as a control experiment to hypercapnia. Each subject will hyperventilate for 1-2 minutes and scans of the subject's eye will be made prior to hyperventilation and during the last 30 seconds of hyperventilation. As the opposite of hypercapnia, hyperventilation decreases sympathetic nervous system activity, leading to increased choroid VPD.

4) Hand grip exercise stimulates the muscle metabolite and mechanical sensors and, due to the sustained contraction, acts as a strong sympathetic nervous system stimulus independent of changes in blood gases. For the testing protocol, subjects produce a sustained contraction (e.g., 30% of predetermined maximal voluntary contraction). Subjects will hold this for a set duration (e.g., 3 minutes). Scans of the subjects' eyes will be taken prior to contraction and during the last 30 seconds of contraction. Since this stimulus leads to increased sympathetic nervous system activity, it produces reduced choroid VPD.

5) The cold pressor test is a general sympathetic stimulus which stimulates pain receptors. Subjects will immerse their non-dominant hand in an ice cold (1-2° C. water bath) for 5 minutes. Scans will be taken prior to and during the last 30 seconds of hand immersion. This stimulus increases sympathetic nervous system activity and, as such, leads to lower choroid VPD.

6) Antagonist drugs. Using a combination of receptor antagonist drugs, the effects of the sympathetic nervous system on different receptors can be isolated. This way, an analysis of the sympathetic nervous system's effects on the choroid can be performed to best characterize how the sympathetic nervous system modulates VPD in the choroid.

Figure 6:
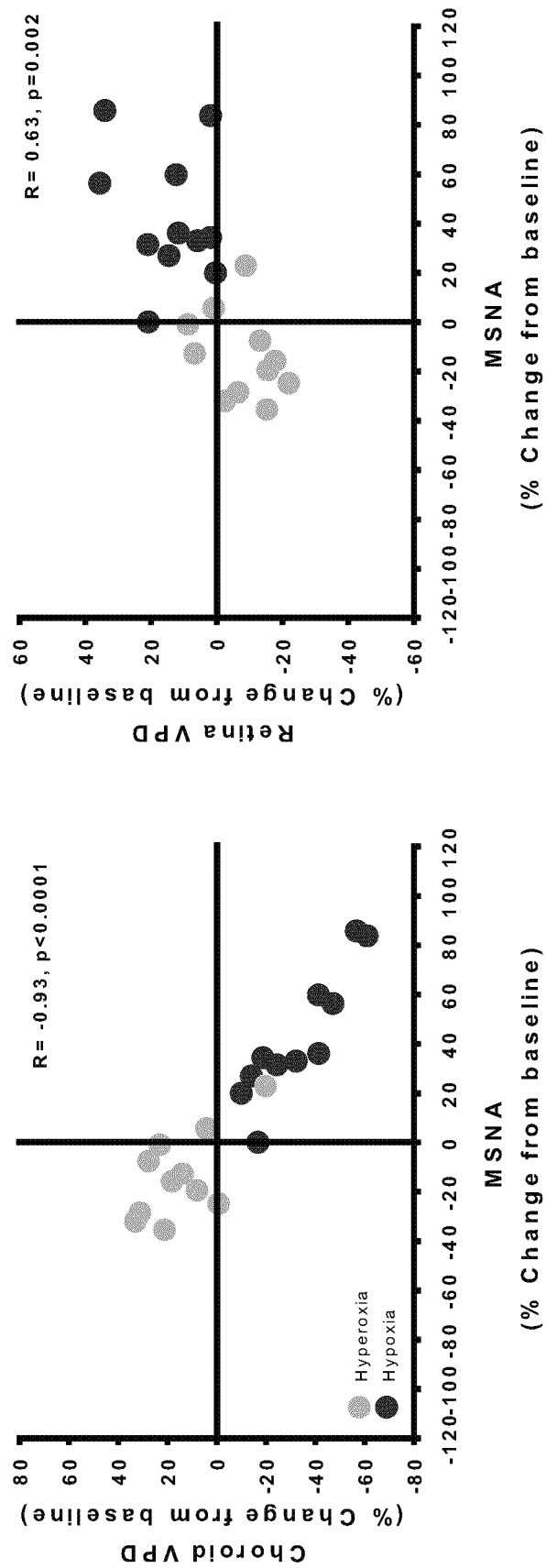
FIG. 6 are graphs demonstrating the divergent responses of the choroid and the retinal layer to stimuli which increase and decrease sympathetic activity.

The differences in tissue beds which are predominantly under autoregulatory control versus tissues which are dominated by the sympathetic nervous system are demonstrated in FIG. 6. The measurements in FIG. 6 were obtained by microneurography in awake humans from the right fibular (peroneal) nerve, posterior to the fibular head. A fine tungsten need electrode is inserted into the nerve and maneuvered to discriminate sympathetic activity. A second needle electrode is used as a reference. The needles are connected to a high impedance amplifier and activity recorder on a computer. MSNA activity was analyzed using custom software.

FIG. 6 illustrates that the choroid shows a reduction in VPD in response to hypoxia (increase in sympathetic activity) and an increase in VPD in response to hyperoxia (reduced sympathetic activity). In comparison, the retinal layer demonstrates the opposite effect such that the metabolic need (a driver of autoregulatory responses, i.e., the surrounding environment) dictates epiretinal VPD. During hypoxia (a state of heightened metabolic demand) epiretinal VPD increases. In contrast, during hyperoxia (a state of reduced metabolic demand) retinal VPD is reduced.

In one embodiment the present invention involves using OCT to simultaneously image vasculature in two or more regions of the eye. The vasculature can then be measured. A mathematical combination of such measurements can then be calculated. Simple examples of this combination include calculating the ratio of the measurements or the difference of the measurements. This mathematical combination of the measurements can be compared before and after relevant stimuli or other interventions to characterize sympathetic nervous system activity or autoregulation. Of particular convenience is the OCT measurement in the choroid and the epiretinal layers because they can be simultaneously measured with the same apparatus.

It should be noted that, for the images illustrated in the Figures, the data initially collected were static images of the eye. A 6(width)×6(height)×2(depth) mm cube of the eye was attained with a 15 μm transverse and a 5 μm axial resolution with 1024 data points per scan using the Cirrus HD OCT device noted above. The cube is bordered with vitreous superficial to the retina and the posterior choroid and is centered on the fovea.

In terms of viewing the image, the mode used with the device noted above is the scan mode, utilizing the advanced visualization parameter and RPE Slice. Slice thickness and distance from retina/optic disk are determined from vessel borders within the choroid slice. The analysis of the slice is then completed by thresholding the image to black and white and attaining pixel density. As an internal control the RGB pixel density and taken as a percentage of blue over all colors confirms thresholded images.

An automated process may be used when comparing baseline choroid images with post stimuli choroid images. For such a process, each post stimulus image may need to undergo image processing steps to ensure that the post stimulus image is suitable for comparison with the baseline image. Accordingly, image processing steps, which may include image translation, image rotation, image reduction, image enlargement, and image registration (i.e., ensuring that the post stimulus image registers with the baseline image so that similar areas are represented in the images) may be taken. In addition, image enhancement or color enhancement steps, including contrast adjustment, contrast or color enhancement, and/or color switching may also be taken. Once the post stimulus images have been processed, color and/or pixel depth as well as color or pixel density may be measured for both the baseline and the post stimulus images. The pixel depth and/or the pixel density may be used as the point of comparison between the baseline and the post stimulus images. As noted above, color images may have their colors converted/adjusted or the color images may be converted to black and white images, if necessary, to determine pixel density. Once pixel densities for the baseline image and for the post stimulus images have been calculated, these numbers may be compared to determine choroid VPD. Of course, a darker post stimulus image (i.e., having a higher pixel density than the baseline image) would indicate that the stimulus produces higher VPD due to lower sympathetic nervous system activity. Similarly, a lighter post stimulus image (i.e., having a lower pixel density than the baseline image) would indicate that the stimulus produces lower choroid VPD due to higher sympathetic nervous system activity.

Figure 7:
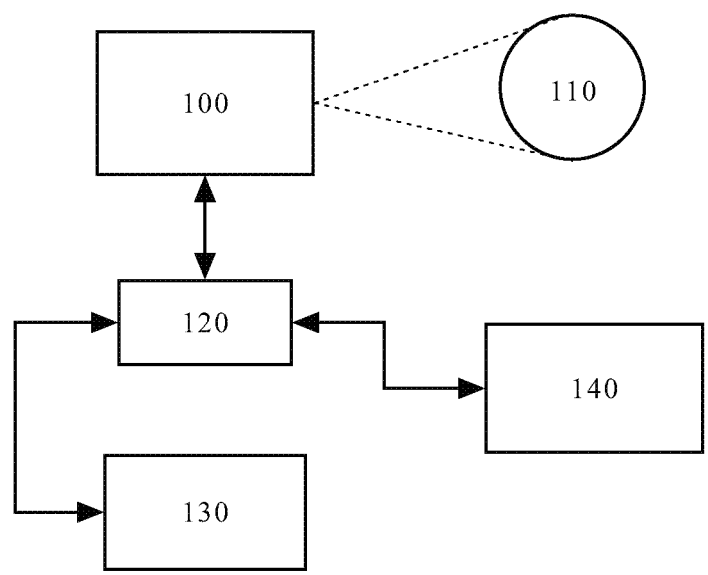
FIG. 7 is a block diagram of a system for use in processing choroid images.

For the above automated process, a system such as that illustrated in FIG. 7 may be used. As can be seen in FIG. 7, the system may include the imaging device 100 that images the human eye 110. Once an image of the eye has been produced, the image is then stored in a storage device 120. The image can then be processed by an image processing block 130. Image processing can take the form of image translation, rotation, enhancement, color adjustment, color substitution, as well as other image processing steps. Preferably, the image processing steps are used to ensure that the image and its contents are suitable for within image comparison and measurement and for comparison with a baseline image or with images previously acquired. The processed image is then stored again in the storage device 120. From the storage device 120, an image comparison block 140 can retrieve the processed image as well as a processed baseline image or other previously processed and previously acquired images. The image comparison block 140 can then extract data from the retrieved images so that the extracted data sets can be compared. As noted above, one data set from the processed image may be the pixel density of the choroid area as a representation of the vascular perfusion density for the area. The extracted data sets (e.g., the pixel densities of the choroid area for the baseline image and the acquired image) can then be compared to non-choroid regions and/or to each other to determine whether the newly acquired image indicates an increase or a decrease in sympathetic nervous system activity or if the newly acquired image indicates little or no change in the sympathetic nervous system activity.

Figure 8A:
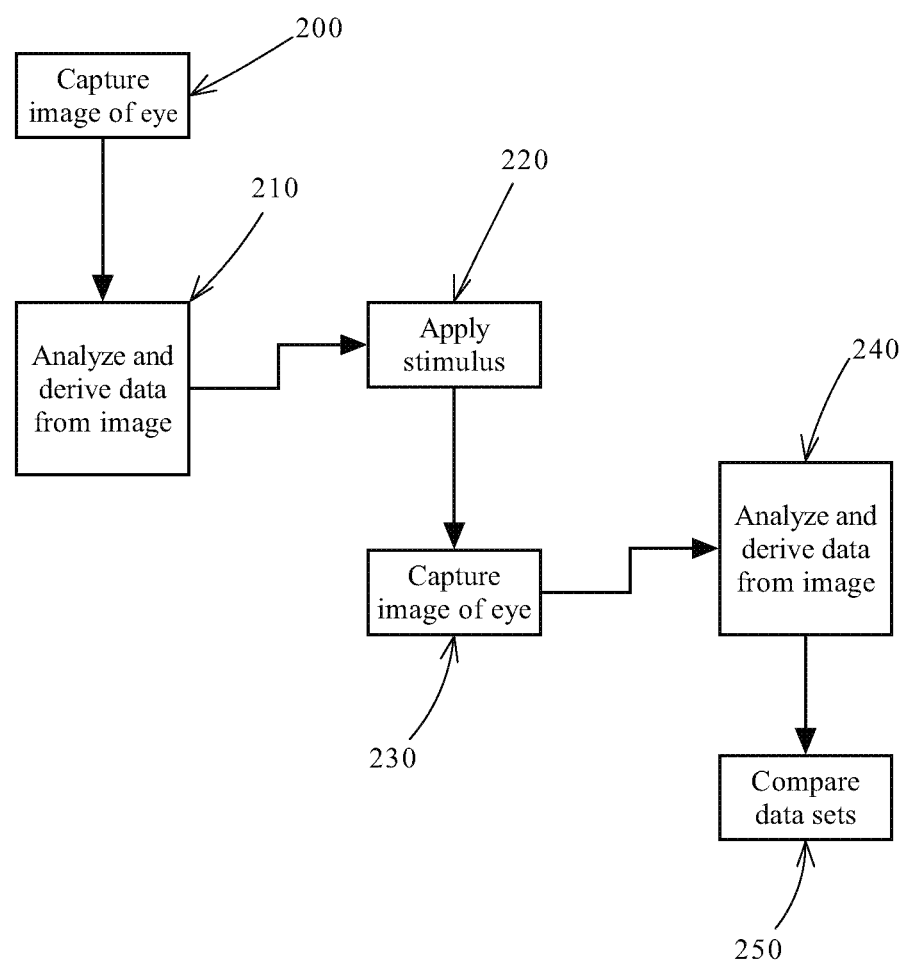
FIG. 8A is a flowchart detailing the steps in a method according to another aspect of the invention.

In another aspect, the invention may take the form of a method for determining the effects of a stimulus on an individual using that individual's choroid. Referring to FIG. 8A, a block diagram illustrating the steps in this method is illustrated. The method may be initiated with the image capture of the individual's eyeball, with particular attention being paid to the choroid of the eye (step 200). Once the image has been captured, the image is then analyzed and the parameters regarding the eye (and in particular the choroid) are derived (step 210). This step, as noted above, may include performing image processing steps on the image to assist in the extraction of data from the processed image. Once the image has been processed, the data can then be extracted. In one example, the data may include a measure of the vascular perfusion density for the choroid. In another example, the data may include a measure of the vascular perfusion density for the choroid and non-choroid region that are differentially regulated by the sympathetic nervous system and autoregulation. The next step in the process may be the application of one or more stimuli on the individual (step 220). The stimulus can be physical, physiological, mental, and/or psychological. After the stimulus has been applied, an image of the individual's eye is once again taken (step 230). As with step 200, particular attention is given to the choroid of the eye. The post stimulus image is then processed and data is extracted in much the same way as in step 210 (step 240). With data extracted from the processed post stimulus image, this extracted data is then compared with the data extracted in step 210 (step 250). The differences in the data sets can be used to determine what effects the stimulus had on the individual's physiology as evidenced by changes to the individual's choroid in reference to itself, or to other parts of the eye that have a difference balance of autoregulatory and sympathetic control. Optionally, the data extracted in step 240 can also be compared with other data sets previously extracted from other individuals.

The steps in the above method can be used to screen patients for sympathetic nervous activity and/or autoregulation. In a clinical setting, the steps in the method can form part of a pre-screening process to identify patients with abnormal sympathetic nervous activity and/or abnormal autoregulation. With disease history and knowledge of sympathetic activity, patients may be better treated with personalized medicine.

The present invention may also be used as part of pharmaceutical research and development as a method to conveniently monitor sympathetic activity/autonomic regulation of subjects enrolled in research projects and/or clinical trials. The use of such a method may reduce the number of drugs that proceed to late-stage trials only to fail because of unexpected cardiovascular complications. As well, the present invention may be used to conduct "sympathetic/autoregulatory phenotyping" as this increases the prospect of personalized medicine, furthering research and development into medications that may be beneficial to a specific phenotype but detrimental to others. These and other benefits may be the result of the present invention as the present invention allows for quick and easy assessment of key cardiorespiratory determinant.

Further studies and analysis have shown the correlation between different stimuli and VPD. For these studies, both choroid and retina VPD (noted as being a static index of perfusion within the image) were calculated for participants before and after stimuli were applied. For the retina, images of the retina were attained from the 3D visualization mode and a 2D flattened image was selected in order to attain the aggregate vasculature of the retinal circulation. The results of these further studies can be seen in the Figures described below.

Figure 8B:
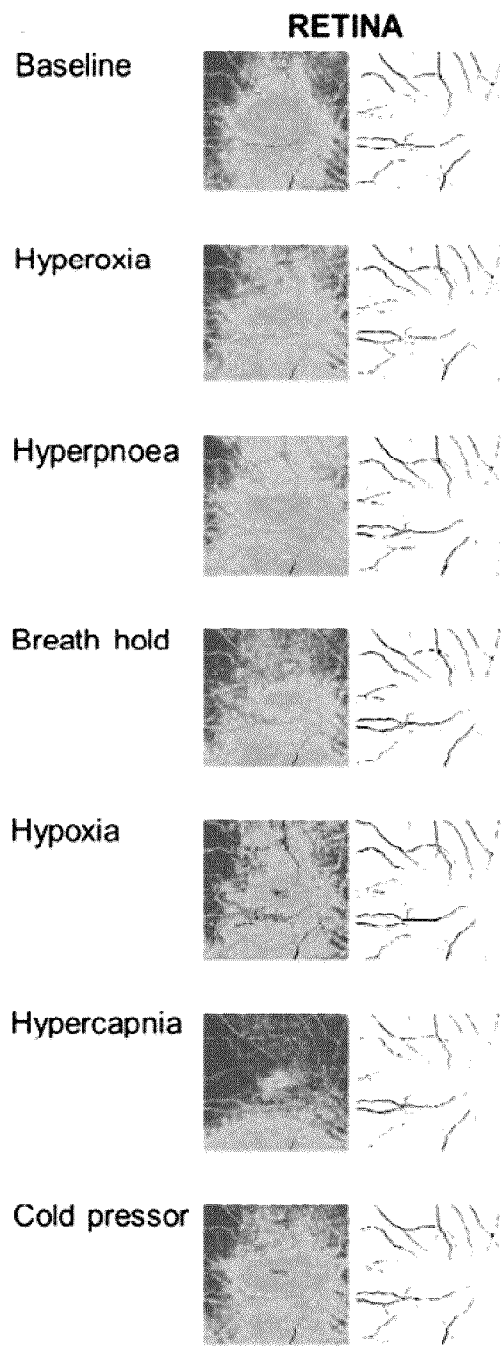
FIG. 8B show raw images and processed images of an individual's retina during baseline and various cardiorespiratory stimuli/challenges.

Referring to FIG. 8B, illustrated are raw images (left column) and processed images (right column) for an individual participant for the retina during baseline and various cardiorespiratory stimuli/challenges (noted next to the relevant image). Vascular perfusion is false colored in the raw images where blue and red represent high and low vascular perfusion, respectively. Retina VPD is demarcated by black pixels in the processed black and white images.

Figure 9A:
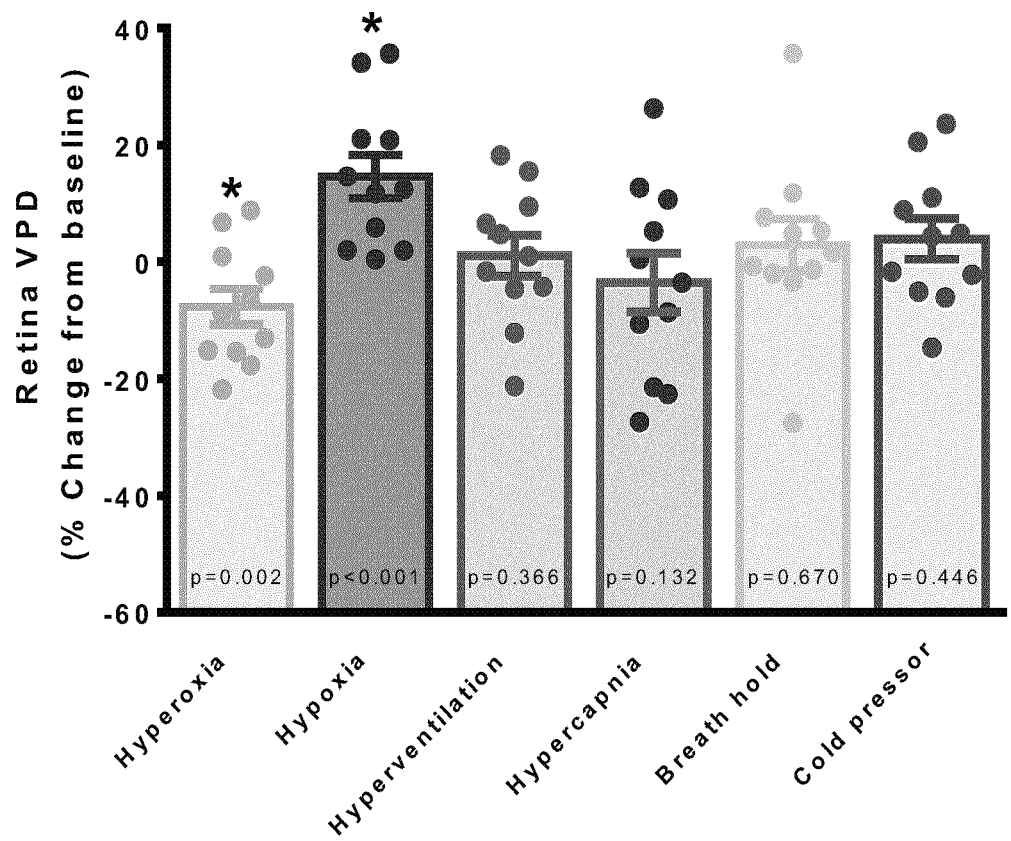
FIG. 9A is a plot showing the change from baseline of retina VPD due to different stimuli.
Figure 9B:
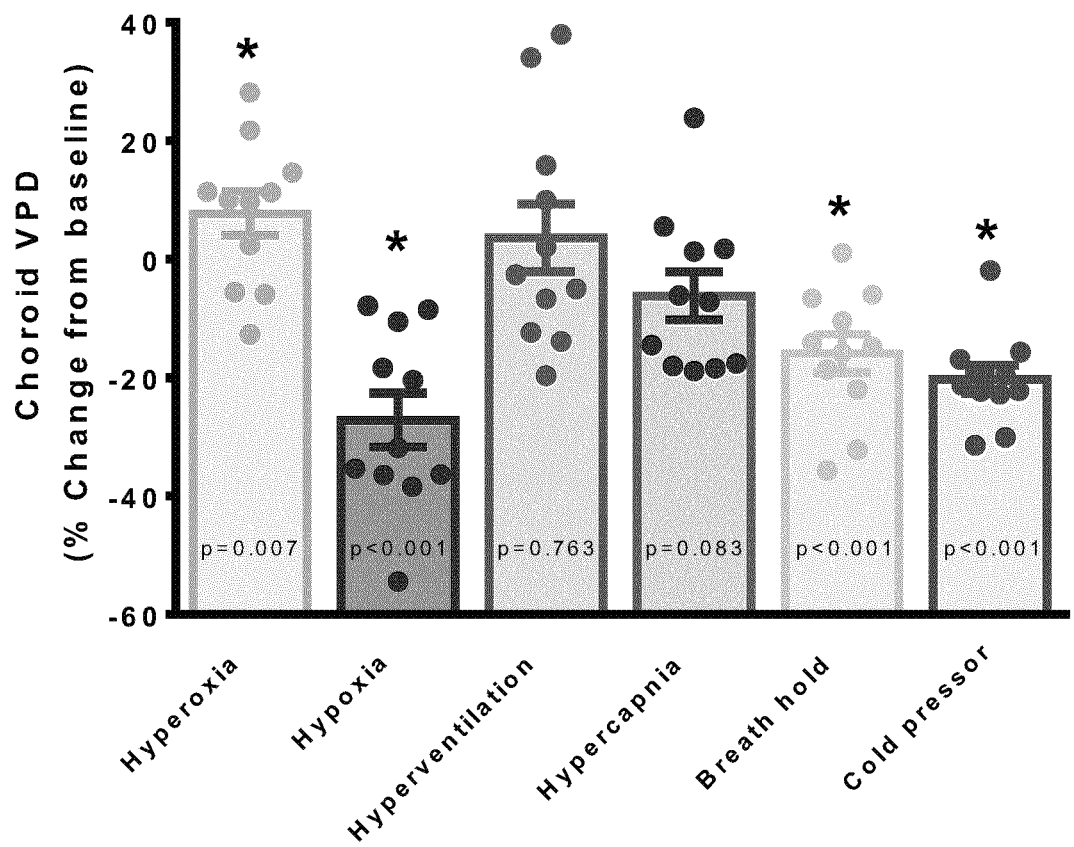
FIG. 9B is a plot showing the change from baseline of choroid VPD due to different stimuli.
Figure 9C:
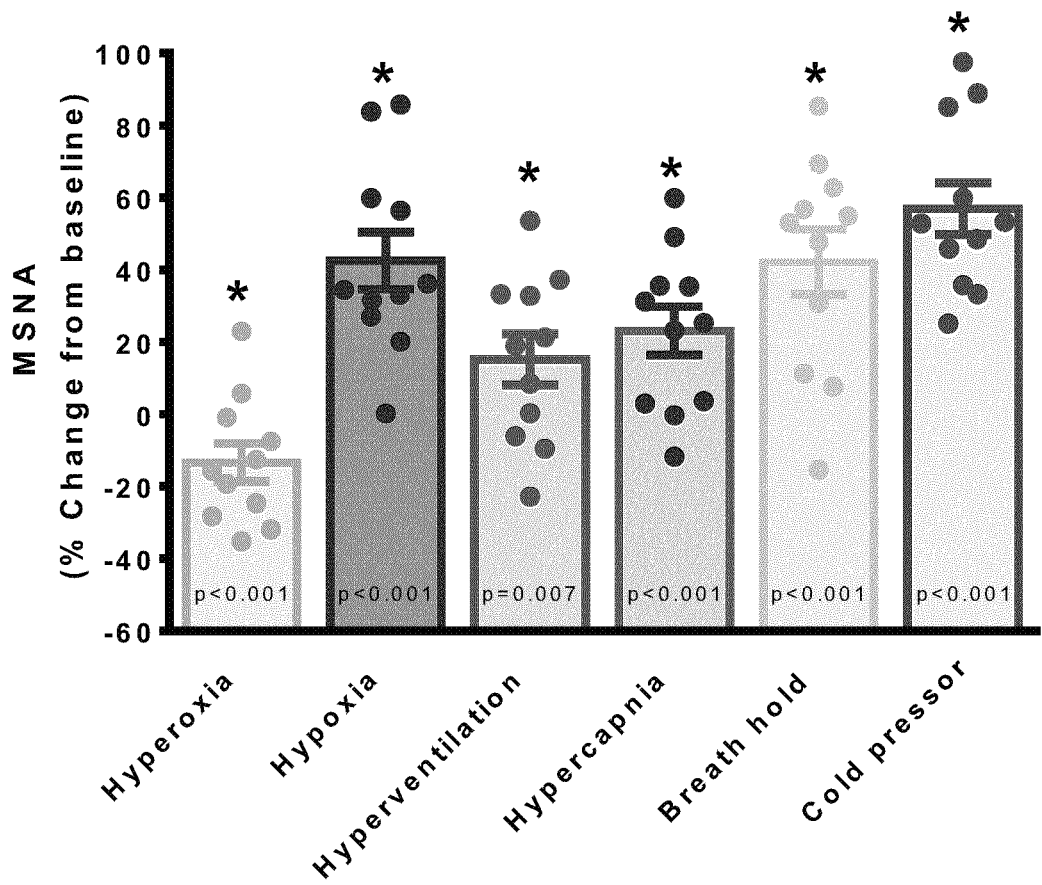
FIG. 9C is a plot showing the change in muscle sympathetic nervous due to different stimuli.

Referring to FIG. 9A, the plot shows the change from baseline of choroid VPD due to different stimuli. As can be seen, for these tests, the stimuli were hyperoxia, hypoxia, hyperpnoea, hypercapnia, breath hold, and cold pressor test. All the data in FIG. 9A are presented as a percentage change from baseline. FIG. 9B shows the change from baseline of retina VPD after the same set of stimuli used for FIG. 9A. FIG. 9C shows the muscle sympathetic nervous activity (MSNA) in response to the same stimuli used for FIGS. 9A and 9B.

Figure 10A:
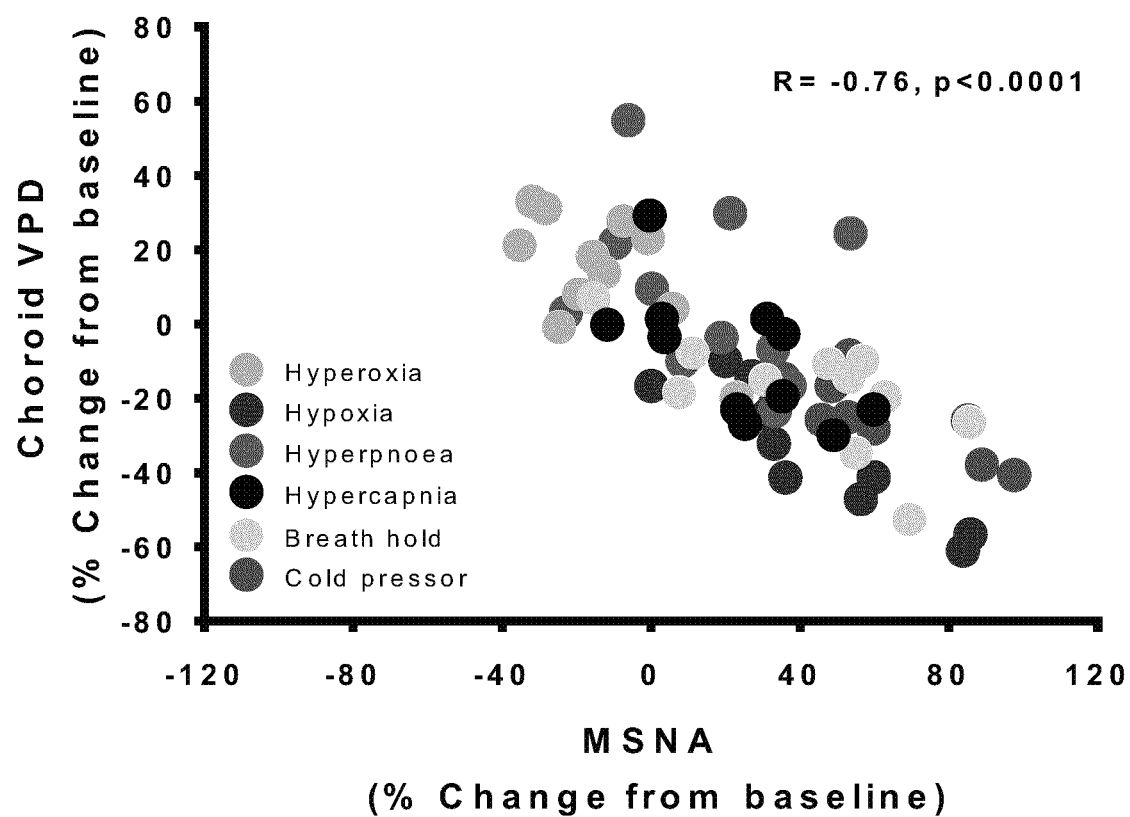
FIGS. 10A-10D show the relationships between choroid VPD, retina VPD, muscle sympathetic nerve activity (MSNA), and mean arterial pressure (MAP)
Figure 10B:
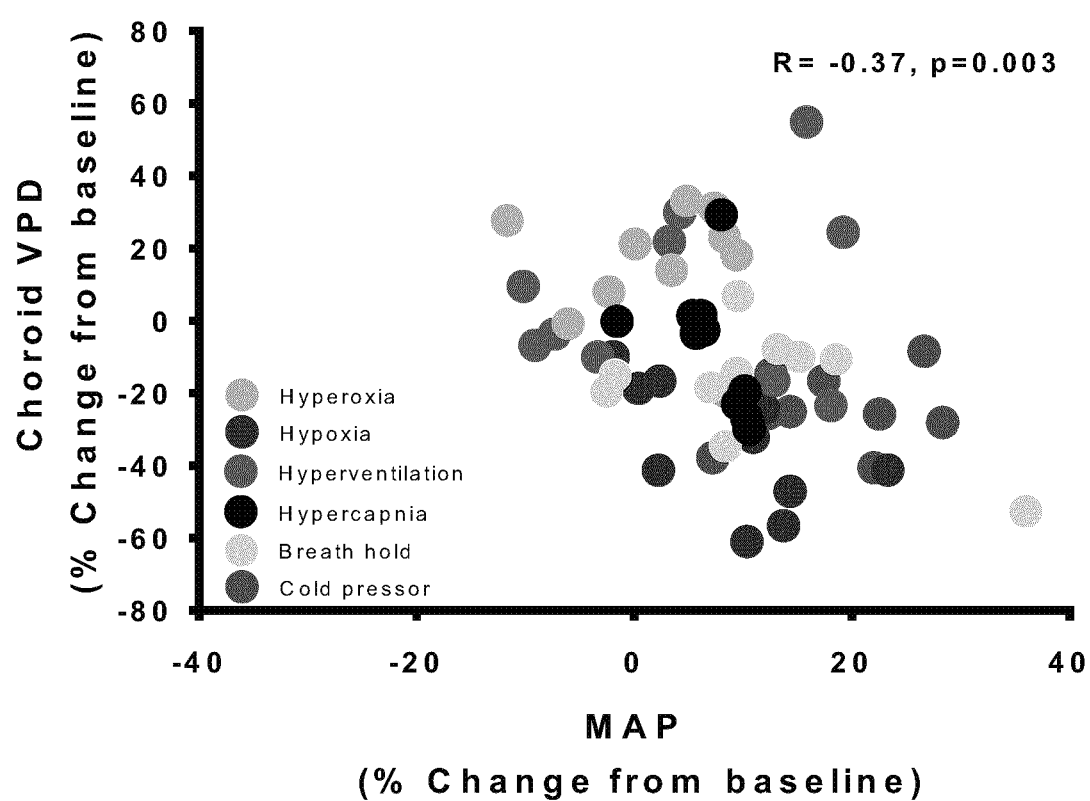
Figure 10C:
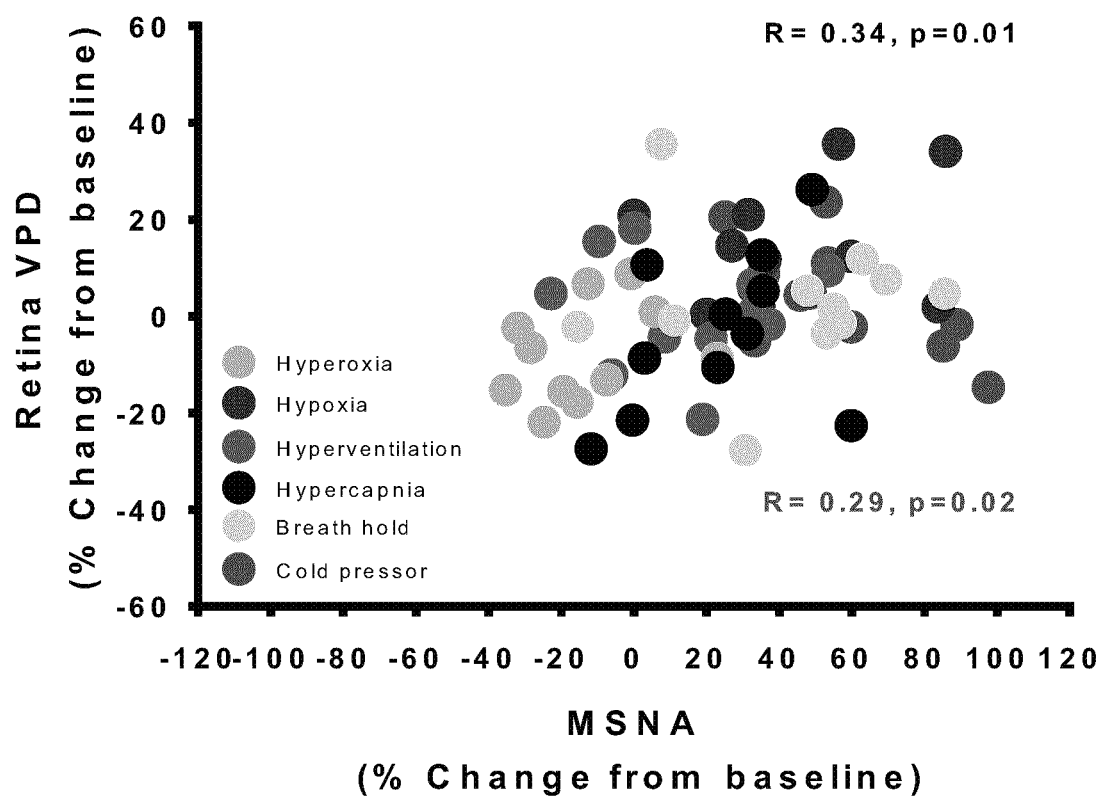
Figure 10D:
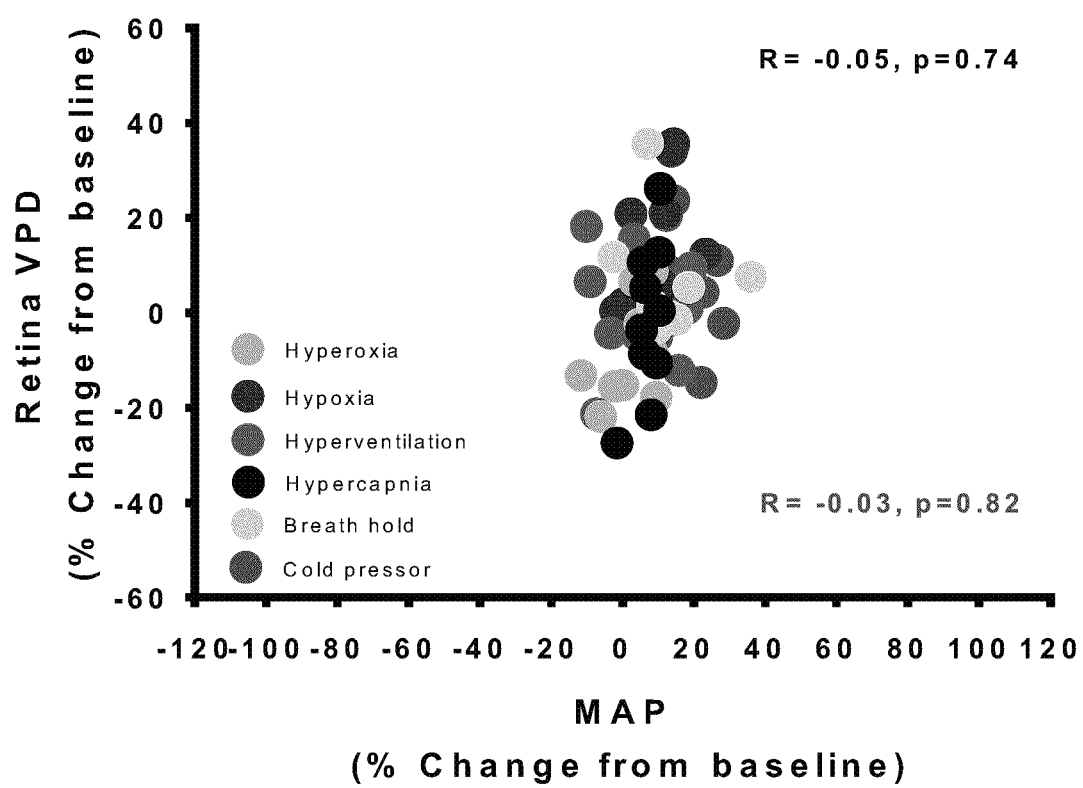

In addition to the above, FIGS. 10A-10D show the relationships between choroid VPD, retina VPD, muscle sympathetic nerve activity (MSNA), and mean arterial pressure (MAP). For these Figures, each data point represents a participant's response to hyperoxia, hypoxia, hyperpnoea, hypercapnia, breath hold, and cold pressor test. FIG. 10A shows the relationship between choroid VPD and MSNA. FIG. 10B shows the relationship between choroid VPD and MAP. FIG. 10C shows the relationship between retina VPD and MSNA while FIG. 10D shows the relationship between retina VPD and MAP. For clarity, Pearson R correlation coefficients with accompanying p-values are indicated for each panel. For relationships involving the retina, values in grey text are inclusive of results for the cold pressor test and values in black text exclude results for the cold pressor test.

Figure 11A:
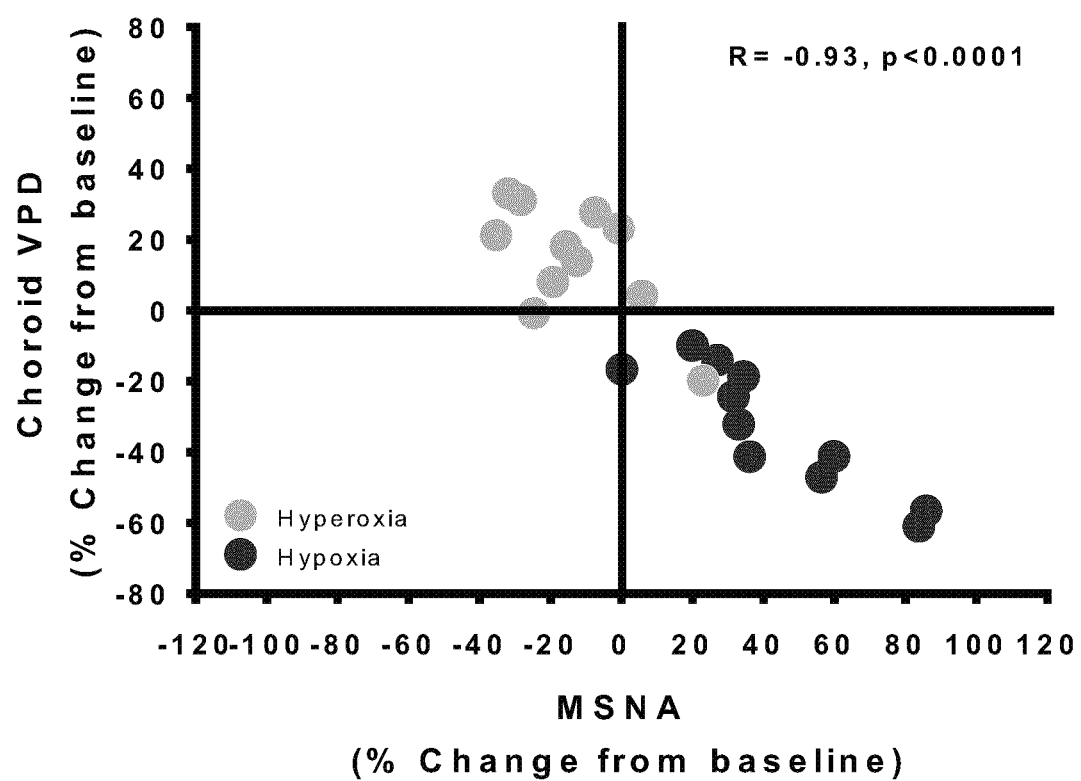
FIGS. 11A-11C are plots of choroid VPD and retina VPD against MSNA and against each other.
Figure 11B:
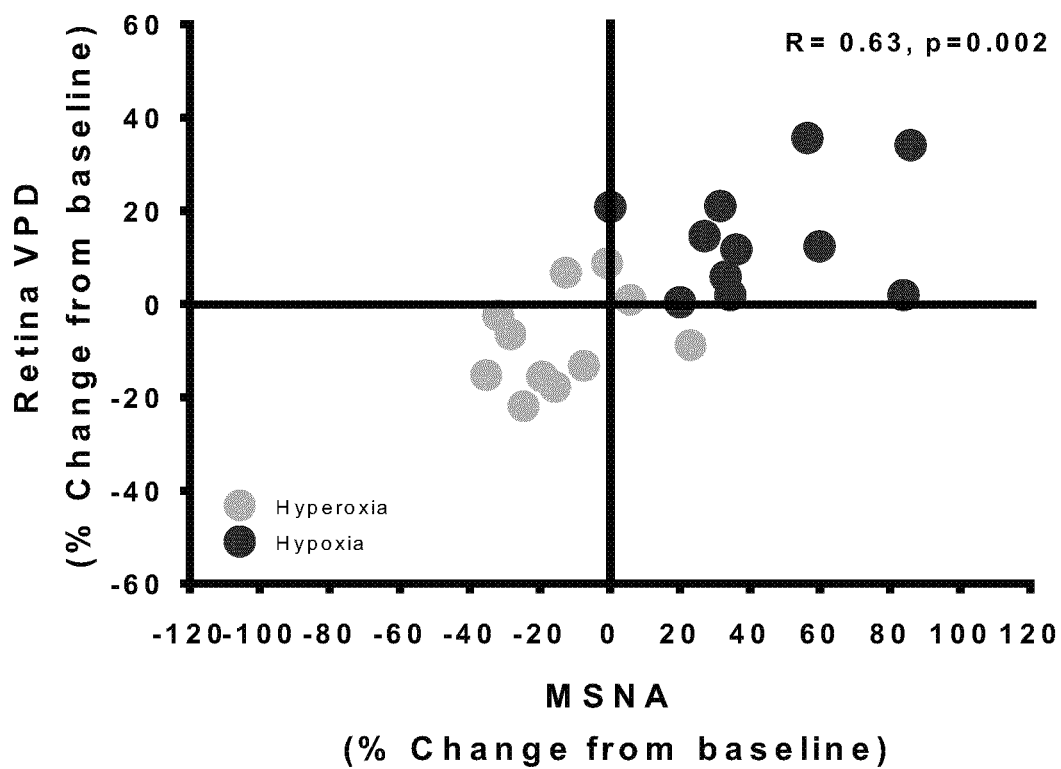
Figure 11C:
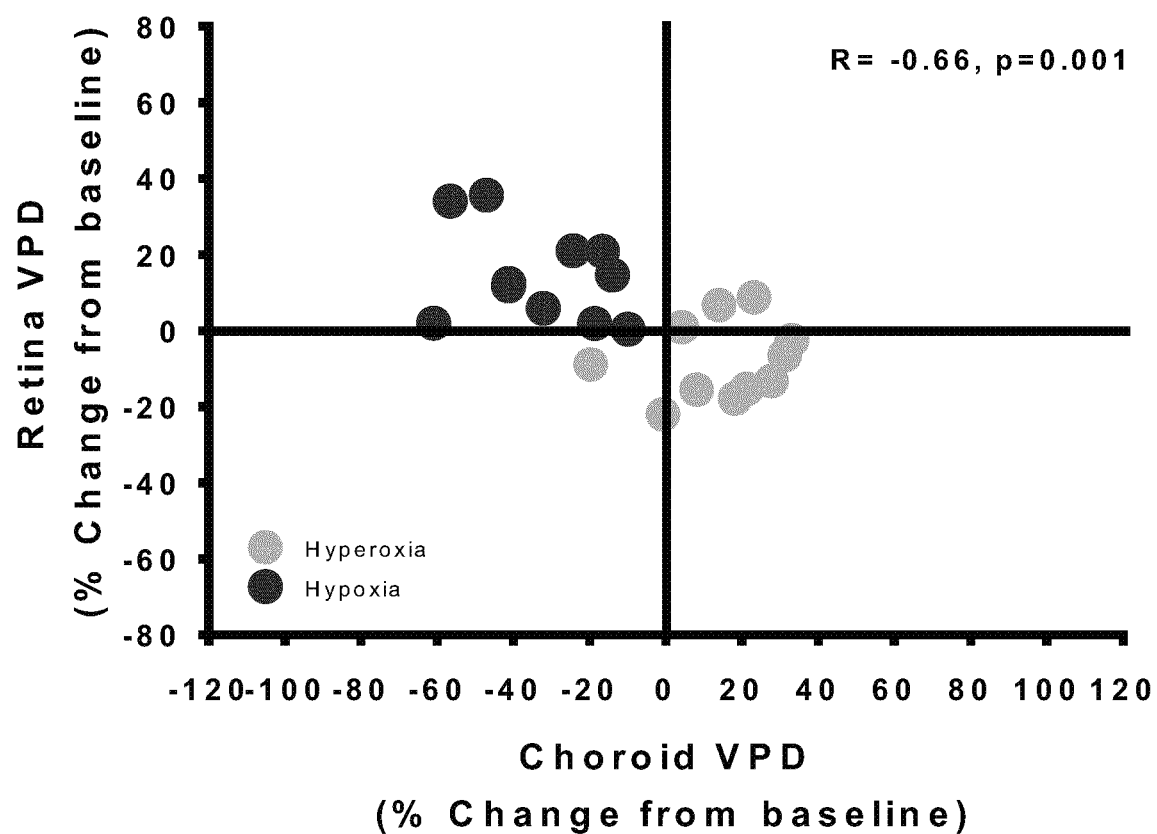

Referring to FIGS. 11A-11C, choroid VPD and retina VPD are plotted against MSNA when the stimuli are hypoxia and hyperoxia. These plots show that the divergent vascular regulatory mechanisms of the choroid (sympathetically regulated) and retina (local vascular regulation) are underscored by the divergent relationships with sympathetic activity. For clarity, the plots are based on percentage change of MSNA from baseline. FIG. 11A plots choroid VPD against MSNA while FIG. 11B plots retina VPD against MSNA. FIG. 11C shows the relationship between retina VPD and choroid VPD and it can be seen that this plot supports the use of choroid VPD as a surrogate measure of MSNA.

Figure 12A:
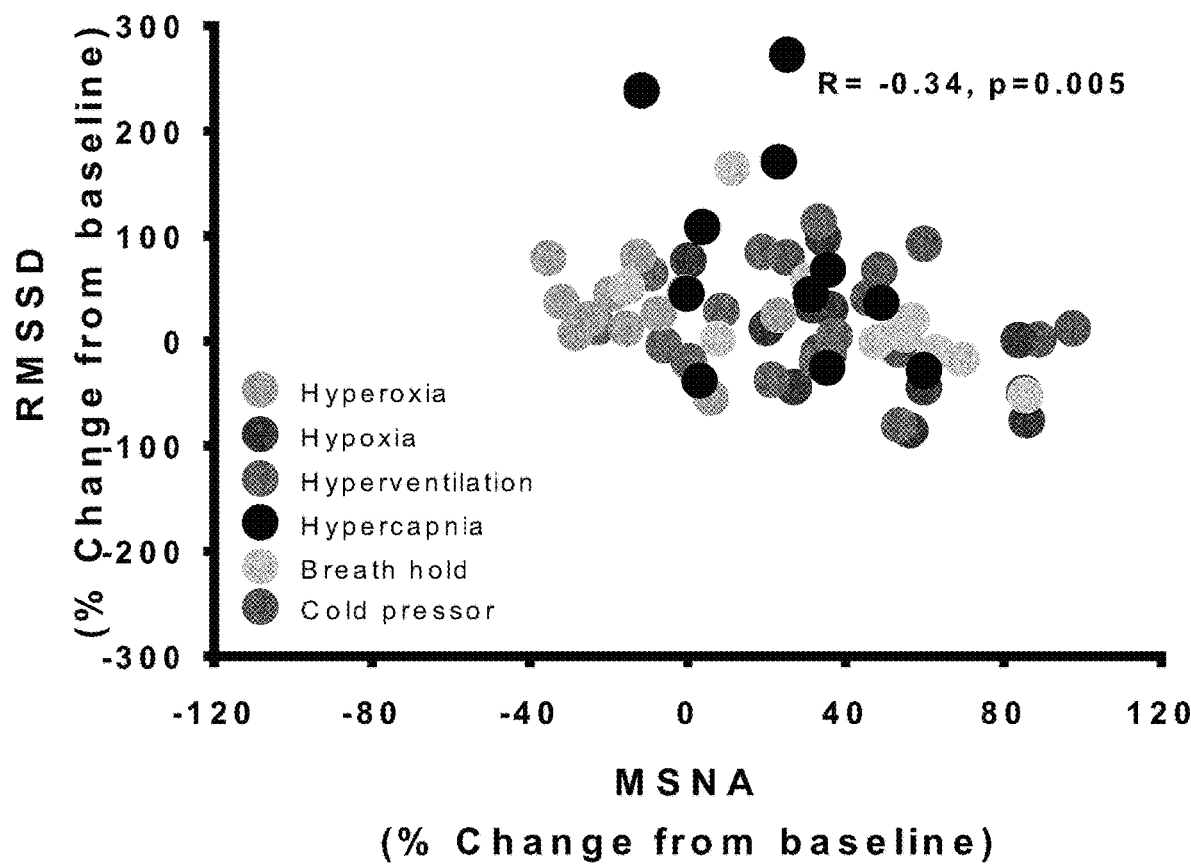
FIGS. 12A-12C are plots detailing the relationship between R-R intervals to muscle sympathetic nervous activity (MSNA).
Figure 12B:
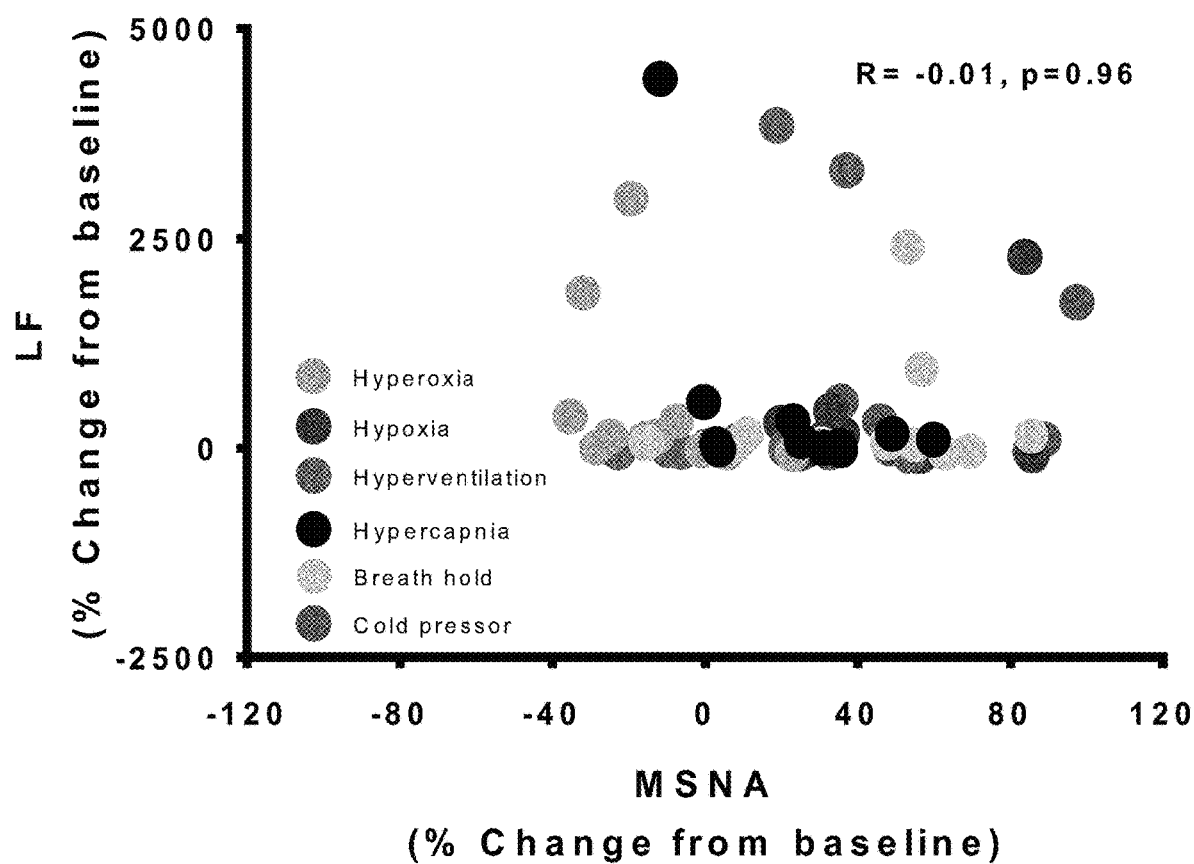
Figure 12C:
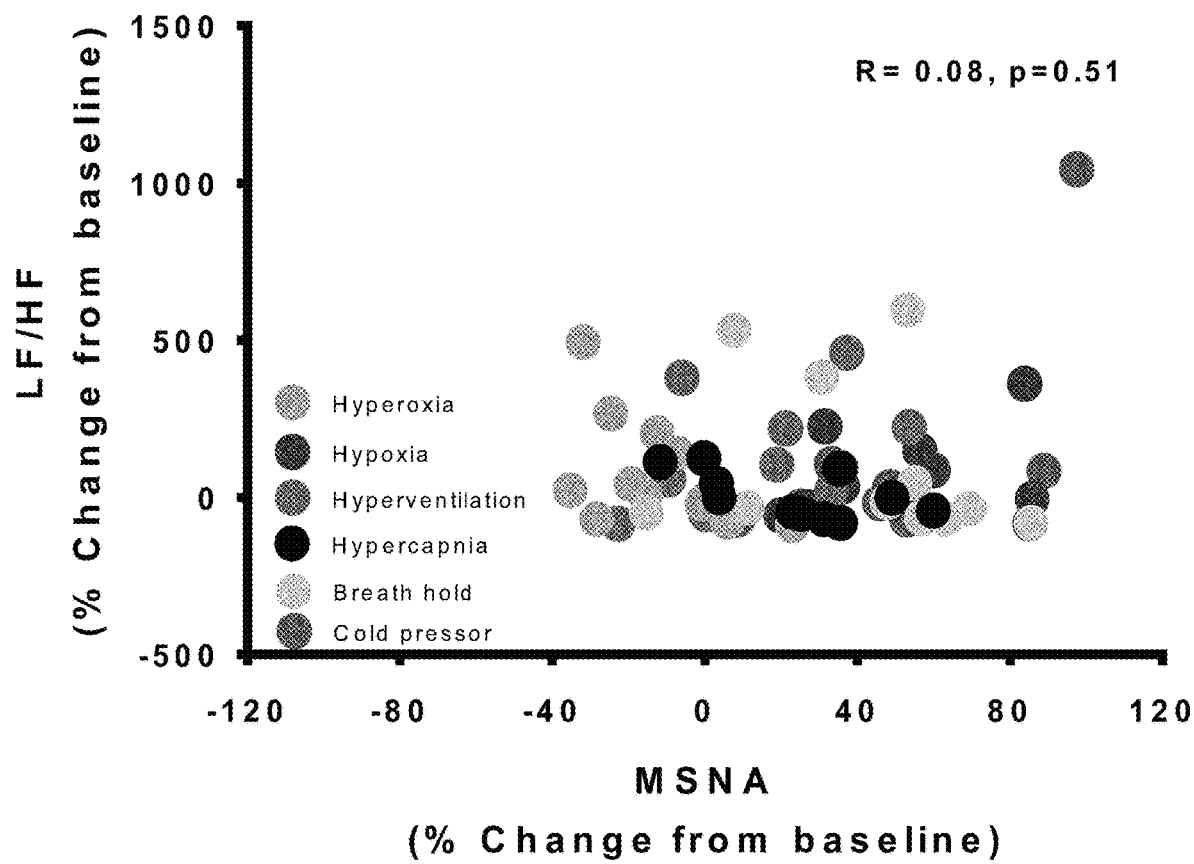

Referring to FIGS. 12A-12C, illustrated are plots detailing the relationship between R-R intervals to muscle sympathetic nervous activity (MSNA). For these plots, each data point represents a participant's response to hyperoxia, hypoxia, hyperpnoea, hypercapnia, breath hold, and the cold pressor test as a percentage change from baseline. FIG. 12A shows the relationship between root mean square of standard deviation R-R interval (RMSSD) to MSNA in response to sympathetic provocations (i.e., stimuli). FIG. 12B shows the relationship of low frequency R-R interval attained from Fast Fourier Transform (LF) to muscle sympathetic nervous activity (MSNA) in response to sympathetic provocations/stimuli. FIG. 12C shows the relationship of low frequency to high frequency R-R interval ratio attained from Fast Fourier Transform (LF/HF) to muscle sympathetic nervous activity (MSNA).

While the above description focuses on optical coherence tomography for imaging an individual's eye, other technologies and techniques which allow for similar imaging results may also be used. As long as a technology or a technique allows for the imaging and/or characterization of an individual's choroid vascular system, it may be used with the present invention. The present invention may also be used with any manoeuvre or intervention (such as a drug treatment) that can activate or suppress the sympathetic nervous system or alter autoregulation. The method of the invention may also be used to identify and characterize manoeuvres and/or interventions previously unknown for its effect on the sympathetic nervous system and autoregulation. If such a manoeuvre or intervention with a previously unknown effect on the sympathetic nervous system/autoregulation is found, the present invention can also be used to identify and characterize manoeuvres or interventions that can counter or aggregate the effect of this manoeuvre or intervention with the previously unknown effect on the sympathetic nervous system/autoregulation.

The present invention may also be used for the development of new drugs targeting sympathetic abnormalities to treat hypertension, hypotension, COPD, asthma and other cardiorespiratory diseases. The development of personalized therapies, targeted to specific cardiorespiratory phenotypes, enhanced subject selection, and phenotyping prior to clinical trials may also benefit from the use of the present invention. Finally, the present invention may be used for earlier detection of unforeseen deleterious cardiorespiratory effects during clinical trials.

The embodiments of the invention may be executed by a computer processor or similar device programmed in the manner of method steps, or may be executed by an electronic system which is provided with means for executing these steps. Similarly, an electronic memory means such as computer diskettes, CD-ROMs, Random Access Memory (RAM), Read Only Memory (ROM) or similar computer software storage media known in the art, may be programmed to execute such method steps. As well, electronic signals representing these method steps may also be transmitted via a communication network.

Embodiments of the invention may be implemented in any conventional computer programming language. For example, preferred embodiments may be implemented in a procedural programming language (e.g., "C") or an object-oriented language (e.g., "C++", "java", "PHP", "PYTHON" or "C #"). Alternative embodiments of the invention may be implemented as pre-programmed hardware elements, other related components, or as a combination of hardware and software components.

Embodiments can be implemented as a computer program product for use with a computer system. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or electrical communications lines) or a medium implemented with wireless techniques (e.g., microwave, infrared or other transmission techniques). The series of computer instructions embodies all or part of the functionality previously described herein. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink-wrapped software), preloaded with a computer system (e.g., on system ROM or fixed disk), or distributed from a server over a network (e.g., the Internet or World Wide Web). Of course, some embodiments of the invention may be implemented as a combination of both software (e.g., a computer program product) and hardware. Still other embodiments of the invention may be implemented as entirely hardware, or entirely software (e.g., a computer program product).

A person understanding this invention may now conceive of alternative structures and embodiments or variations of the above all of which are intended to fall within the scope of the invention as defined in the claims that follow.

We claim:

1. A system for determining differences in sympathetic nervous system activity in a first human subject, the system comprising:
    an imaging device for imaging at least one portion of a human eye of said first human subject, said imaging device producing at least one image of said at least one portion of said human eye;
    a data storage device for storing baseline data from at least one previously obtained baseline image of the human eye of said first human subject and for storing said at least one image;
    a data processor for processing said at least one image and for extracting data from said at least one image;
    wherein
        said data storage device stores said at least one image from said imaging device;
        said data processor compares data extracted from said at least one image with said baseline data;
        said data extracted from said at least one image is a pixel density or a voxel density of said at least one image;
        said baseline data is pixel density or voxel density of said at least one previously obtained baseline image;
        prior to said data being extracted from said at least one image, said at least one image undergoes color switching, a degree of said color switching for said at least one image being determined by said data processor based on said baseline data, such that, after said color switching, said data extracted from said at least one image is suitable for comparison with said baseline data;
        said at least one portion comprises choroid vasculature of said human eye; and
        said pixel density or said voxel density of said at least one image is indicative of vascular perfusion density in said choroid vasculature such that said pixel density or said voxel density of said at least one image is directly related to said sympathetic nervous system activity.

2. The system according to claim 1, wherein said at least one image comprises at least one post-stimulus image.

3. The system according to claim 1, wherein said at least one baseline image further comprises at least one image of a portion of an eye of a second human subject, said first human subject being different from said second human subject.

4. The system according to claim 1, wherein said at least one image is further processed prior to said data being extracted from said at least one image.

5. The system according to claim 4, wherein said at least one image undergoes image processing comprising at least one of: image translation, image rotation, image reduction, image enlargement, and image registration.

6. The system according to claim 4, wherein, prior to said data being extracted, said at least one image further undergoes at least one of: image enhancement, contrast adjustment, contrast enhancement, and color enhancement.

7. A method for determining changes in sympathetic nervous system activity in a first human subject, the method comprising:
    storing baseline data from at least one previously obtained baseline image of a first eye of the first human subject;

obtaining, by way of an Optical Coherence Tomography (OCT) device, at least one image of at least one portion of the first eye of said first human subject, and wherein, after being obtained, said at least one image undergoes color switching, a degree of said color switching for said at least one image being based on said baseline data such that, after said color switching, said at least one image is suitable for comparison with said at least one previously obtained baseline image;

determining a measurement of a vascular perfusion density in said first eye from said at least one image, wherein said vascular perfusion density is measured by measuring at least one of: pixel density or voxel density of said at least one image, said measurement being executed by at least one image processor; and comparing said pixel density or said voxel density of said at least one image to a pixel density or voxel density of said at least one previously obtained baseline image to determine if said sympathetic nervous system activity is increased or decreased, said step of comparing being executed by a data processor, wherein said pixel density or said voxel density of said at least one image is directly related to said sympathetic nervous system activity.

8. The method according to claim 7, wherein said at least one portion comprises choroid vasculature of said first eye.

9. The method according to claim 7, wherein said at least one portion comprises retinal vasculature of said first eye.

10. The method according to claim 7, wherein said at least one image undergoes image processing, said image processing comprising at least one of: image translation, image rotation, image reduction, image enlargement, and image registration.

11. The method according to claim 7, wherein said at least one image further undergoes at least one of: image enhancement, contrast adjustment, contrast enhancement, and color enhancement.

12. The method according to claim 7, wherein said previously obtained baseline image of said first eye is an image of a portion of said first eye that is different from said at least one image.

13. The method according to claim 7, wherein said at least one portion of said first eye comprises a choroid of said first eye and said previously obtained baseline image of said first eye is from a region of said first eye other than said choroid.

14. The method according to claim 7, wherein said at least one portion comprises a retina of said first eye.

15. The method according to claim 7, wherein said at least one previously obtained baseline image further comprises at least one image of a portion of an eye of a second human subject, said first human subject being different from said second human subject.

* * * * *